(12) United States Patent
de la Paz

(10) Patent No.: US 7,632,649 B2
(45) Date of Patent: Dec. 15, 2009

(54) SP1 AS A MARKER IN DIAGNOSIS AND PROGNOSIS OF NON-ALCOHOLIC STEATOHEPATITIS (NASH) AND TARGET IN DRUG SCREENING FOR NASH

(75) Inventor: José María Mato de la Paz, Cizur Menor (ES)

(73) Assignee: One Way Liver Genomics, S.L., Derio-Vizcaya (ES)

( * ) Notice: Subject to any disclaimer, the term of this patent is extended or adjusted under 35 U.S.C. 154(b) by 265 days.

(21) Appl. No.: 11/370,068

(22) Filed: Mar. 7, 2006

(65) Prior Publication Data

US 2006/0205023 A1    Sep. 14, 2006

(30) Foreign Application Priority Data

Mar. 11, 2005 (EP) .................................. 05075602

(51) Int. Cl.
 *G01N 33/53* (2006.01)
(52) U.S. Cl. ..................... 435/7.1; 435/7.2; 435/7.91; 435/7.92
(58) Field of Classification Search .................. 435/7.1, 435/7.2, 7.91, 7.92
See application file for complete search history.

(56) References Cited

U.S. PATENT DOCUMENTS 5,854,254 A * 12/1998 Benoff ......................... 514/277
6,084,072 A *  7/2000 Rinderle et al. ............. 530/370
7,332,299 B2 *  2/2008 Hamilton .................... 435/69.1

FOREIGN PATENT DOCUMENTS

WO         02066071 A       8/2002

OTHER PUBLICATIONS

One Way Liver Genomics, S.L., "European Search Report," May 17, 2006.
Verrecchia et al., "Blocking Sp1 Transcription Factor Broadly Inhibits Extracellular Matix Gene Expression In Vitro and In Vivo: Implications for the Treatment of Tissue Fibrosis," Journal of Investigative Dermatology, vol. 116, No. 5, May 2001, pp. 755-763.
Ihn et al., "Increased Phosphorylation of Transcription Factor Sp1 in Schleroderma Fibroblasts: Association with Increased Expression of the Type I Collagen Gene," Arthritis and Rheumatism, vol. 43, No. 10, Oct. 2000, pp. 2240-2247.
Black et al., "Growth/Cell Cycle Regulation of Sp1 Phosphorylation," Journal of Biological Chemistry, vol. 274, No. 3, Jan. 15, 1999, pp. 1207-1215.
Leggett et al., "Sp1 is Phosphorylated and its DNA Binding Activity Down-Regulated Upon Terminal Differentiation of the Liver," Journal of Biological Chemistry, American Society of Biolochemical BIologists, vol. 270, No. 43, Oct. 27, 1995, pp. 25879-25884.
Lu et al., "Methionine Adenosyltransferase 1A Knockout Mice are Predisposed to Liver Injury and Exhibit Increased Expression of Genes Involved in Proliferation," Proceedings of the National Academy of Sciences of USA, vol. 98, No. 10, (May 8, 2001), pp. 5560-5565.
Chu et al., "Sp1: Regulation of Gene Expression by Phosphorylation," Gene, vol. 348, (Mar. 28, 2005), pp. 1-11.

* cited by examiner

*Primary Examiner*—Jacob Cheu
(74) *Attorney, Agent, or Firm*—Tristan A. Fuierer; Moore & Van Allen, PLLC

(57) ABSTRACT

Phosphorylated Sp1 can be used as a marker for in vitro diagnosis of non-alcoholic steatohepatitis (NASH) as well as a therapeutical target of said condition.

8 Claims, 3 Drawing Sheets

CONTROL  Ip AntiPhosphoserine Blot Anti SP1

Input Blot Anti SP1

NASH  Ip AntiPhosphoserine Blot Anti SP1

Input Blot Anti SP1

US 7,632,649 B2

SP1 AS A MARKER IN DIAGNOSIS AND PROGNOSIS OF NON-ALCOHOLIC STEATOHEPATITIS (NASH) AND TARGET IN DRUG SCREENING FOR NASH

CROSS REFERENCE TO RELATED APPLICATIONS

This application claims priority under 35 U.S.C. §119(a) of European Patent Application No. 05075602.2 for "Sp1 as a Marker in Diagnosis and Prognosis of Non-Alcoholic Steatohepatitis (NASH) and Target in Drug Screening for NASH" filed on Mar. 11, 2005 in the name of JoséMaria Mato de la Paz, which is incorporated herein in its entirety.

FIELD OF THE INVENTION

The invention refers, in general, to in vitro diagnosis of non-alcoholic steatohepatitis (NASH); more specifically to the early diagnosis of NASH and/or to the predisposition of a subject to develop NASH or to confirm the disease, based on an overexpression of phosphorylated Sp1 transcription factor in liver cells. The invention also refers to determine the stage or severity of said disease in an individual, or to monitor the effect of therapy administered to an individual with NASH. Additionally, the invention refers to screen, seek, identify, develop and evaluate the efficacy of compounds for the prevention and/or treatment of NASH in an attempt to develop new medicinal products as well as agents that inhibit the expression and/or activity of Sp1 in liver, and/or the effects of its expression.

BACKGROUND OF THE INVENTION

Non-alcoholic steatohepatitis (NASH) is a progressive disease of the liver of unknown ethiology characterized histologically by fatty acid accumulation, hepatocyte damage and inflammation resembling alcoholic hepatitis. NASH is a critical stage in the process that spans from hepatic steatosis to cirrhosis and liver failure. Obesity and type-2 diabetes are associated to NASH. Since the prevalence of these diseases is increasing, the prevalence of NASH is also expected to increase and therefore, this disease has become an emerging public issue in the United States [Reid A E. Nonalcoholic steatohepatitis. Gastroenterology 2001;121:710-723] as well as in other countries [Farell G C. Non-alcoholic steatohepatitis: what is it, and why is it important in the Asia-Pacific region? J Gastroenterol Hepatol 2003;18:124-138].

NASH is thought to arise from the interaction of many different genes and lifestyle factors. Mitochondrial impairment, oxidative stress and metabolic deregulation, have all been involved in the pathogenesis of steatohepatitis.

As it is true for other complex diseases, the genetic factors contributing to the development of NASH may be more readily identified by combining studies in patients with NASH and in animal models of the disease. One of these models is MAT1A knockout (MAT1A-KO) mice. These mice spontaneously develop NASH and hepatocellular carcinoma at about 8 and 15 months of age, respectively [Lu S C et al. Proc. Natl. Acad. Sci. USA 98:5560-5565 (2001); Martinez-Chantar M L et al. FASEB J 2002, 16(10), page 1292-1294. MAT1A gene encodes for methionine adenosyltransferase I and III, the main enzymes responsible of S-adenosylmethionine (SAMe) synthesis in liver. Earlier studies concluded that patients with liver cirrhosis and alcoholic hepatitis are deficient in SAMe synthesis; and that treatment with SAMe improves survival in patients with alcoholic liver cirrhosis.

Early diagnosis of NASH has been held back by the lack of reliable early markers of NASH development. Identification of genes and proteins expressed differentially in NASH with potential as biological markers or therapeutic targets could lead to the development of new tools for the diagnosis, prognosis and treatment of this disease.

A method for the diagnosis of NASH by using molecular markers based on the proteomic determination of a set of proteins detected in liver tissue samples has been disclosed (WO2004/055520).

Another method for the diagnosis of NASH based on the identification of a cluster of 85 discriminative early gene markers specific of NASH in liver tissue samples (thus, constituting what has been named the "genomic signature or fingerprint of NASH") has been also described by the Applicant (EP 04103540.3). The technique used in that case combines liver samples from MAT1A-KO mice and from patients with early-stage NASH with bioinformatic and statistical methods to analyze the data generated from genome-wide expression profiling of the mentioned liver samples, thus allowing the identification of a cluster of discriminative early gene markers of steatohepatitis in mice and humans. Among the genes comprising the genomic signature of NASH there are enzymes (the majority being hydrolases, transferases and oxidoreductases), ligand-binding genes (heavy metal binding, nucleotide binding, protein binding, receptors and transcription factors); transporters (carbohydrate, electron transporter, and protein transporters); apoptosis regulators; chaperones; blood coagulation factors; and several genes with unknown function.

Looking for the presence of consensus sequences for vertebrate transcription factors among the promoters of the genes listed in Table 1 (EP 04103540.3), the inventors have now, surprisingly, found that only Sp1 transcription factor was present significantly in the promoters of a great number of the genes listed in said Table 1, more than would be expected by chance, suggesting that activation of Sp1 may be involved in the underlying mechanisms that lead to NASH.

Sp1 was one of the first eukaryotic transcription factors to be identified and cloned as a factor binding the SV40 early promoter (Dynan and Tjian, Cell 35:79-87, 1983). It is the founding memder of a family of proteins with highly homologous zinc-finger domains in the C-terminal region that bind GC or GT boxes, while the glutamine rich domains in the N-terminus are essential for transcriptional activation. Sp1 activates transcription by association with one of the co-activators associated with the TATA binding protein (TBP) in the TFIID complex. Other suggested roles for Sp1 in nuclear processes include remodeling of chromatin structures and maintenance of methylation-free CpG islands. Therefore, Sp1 is fundamental for the establishment of transcriptional competence, in addition to its role as a transcription factor. In a majority of promoters containing Sp1 binding sites, Sp1 provides a basal level of transcription. It plays an important role in the expression of numerous elements of the cell-cycle machinery, such as cyclins, Rb-like proteins, and E2F. Targeted disruption of the mouse Sp1 gene has shown that Sp1 is critical for normal embryogenesis. Sp1 (−/−) embryos are severely retarded in their development and display a marked heterogeneity in their phenotype. Interestingly, inactivation of the Sp1 gene is compatible with a certain degree of cell growth and differentiation, and the expression of various putative target genes, including that of certain cell cycle-related genes, was not altered in Sp1 (−/−) embryos. Also, CpG islands remained methylation free and active chromatin was formed at the globin loci. This may occur possibly because other members of the Sp1 family partially compensate for the absence of Sp1, thereby ameliorating the Sp1 knockout. Sp1 is involved in the basal expression of extracellular matrix (ECM) genes and is important in fibrotic processes. Thus, blocking Sp1 inhibits ECM gene expression what can be used in the treatment of fibrotic disorders (WO 02/066701).

DETAILED DESCRIPTION OF THE INVENTION

Definitions

Figure 1:
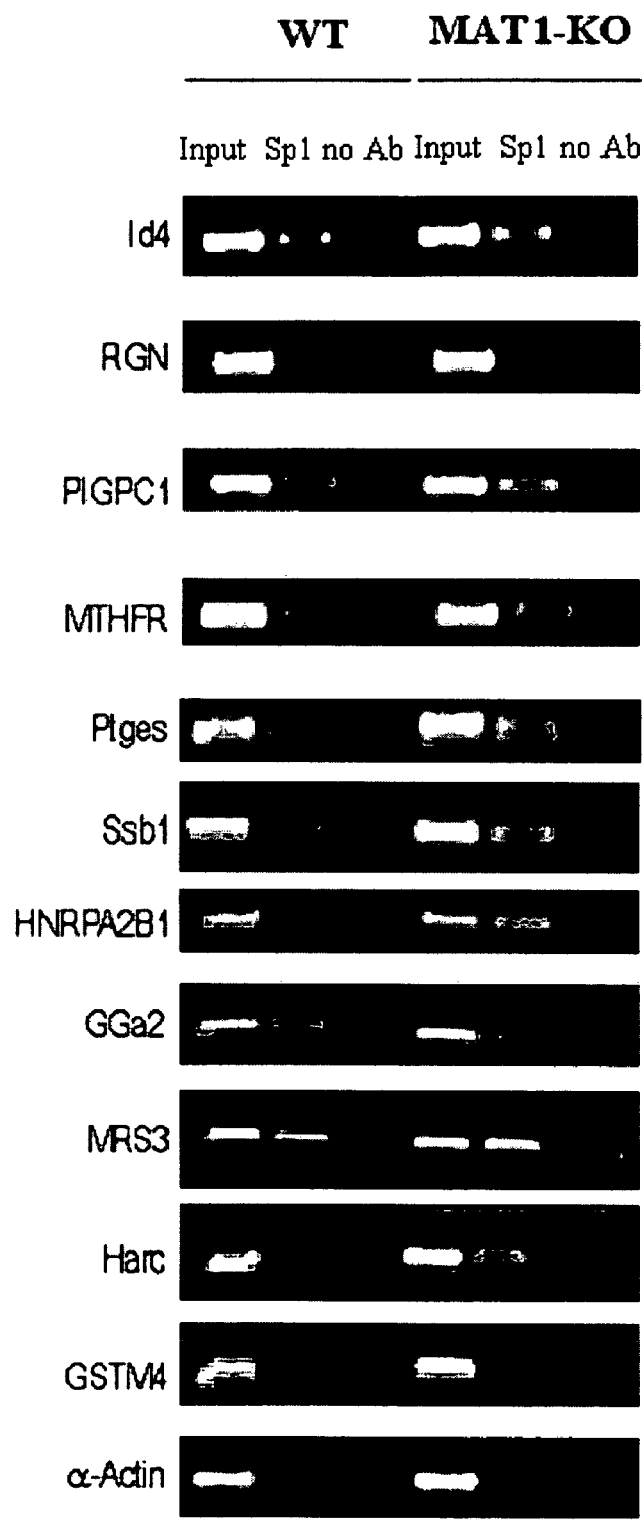
FIG. 1 shows the results of an in vivo binding analysis of Sp1 to selected gene promoters. Immunoprecipitation of formaldehyde-crosslinked chromatin was carried out in liver tissue samples from control mice (Wild Type, WT) and in liver tissue samples from MAT1A-KO mice by using an anti-Sp1 antibody (Example 1). Immunoprecipitates were aliquoted and subsequently analyzed by PCR with primers specific for each gene promoter. In each case, a sample of total chromatin (Input) was included in the PCR reactions. No Ab: No antibody. Sp1: Immunoprecipitation fraction. α-Actin promoter was included as a negative control.

In order to facilitate the comprehension of the present patent application we list below the meaning of some terms and expressions within the context of the invention.

The term "subject" refers to all animals classified as mammals and includes, but is not restricted to, domestic and farm animals, primates and humans. The subject is preferably a male or female human of any age or race.

The term "NASH" refers to non-alcoholic steatohepatitis.

The term "gene" refers to a region of a molecular chain of deoxyribonucleotides that encodes a protein and may represent a portion of a coding sequence or a complete coding sequence.

The term "DNA" refers to deoxyribonucleic acid. A DNA sequence is a sequence of deoxyribonucleotides.

The term "RNA" refers to ribonucleic acid. A RNA sequence is a sequence of ribonucleotides.

The term "mRNA" refers to messenger ribonucleic acid, which is the fraction of total RNA which is translated into protein.

The term "cDNA" refers to a nucleotide sequence complementary to a sequence of mRNA.

The term "nucleotide sequence" refers either to a sequence of ribonucleotides (RNA) or a sequence of deoxyribonucleotides (DNA).

The term "protein" refers to at least one molecular chain of amino acids linked through either covalent or non-covalent bonds. The term includes all forms of post-translational protein modifications, for example glycosylation, phosphorylation or acetylation.

The term "antibody" refers to a glycoprotein that exhibits a specific binding activity for a target molecule called an "antigen". The term "antibody" includes monoclonal and polyclonal antibodies, either intact or fragments derived from them; it also includes human antibodies, humanised antibodies and antibodies of non-human origin. "Monoclonal antibodies" is a homogeneous, highly specific antibody population that can bind to a single antigenic site or "determinant" on the target molecule. "Polyclonal antibodies" is a heterogeneous antibody population that can bind to multiple antigenic sites or "determinants" of the target molecule.

The term "epitope" refers to an antigenic determinant of a protein recognised by a specific antibody. An epitope may consist of a contiguous stretch of amino acids (linear epitope), of non-contiguous amino acids that are brought into proximity with one another by virtue of the three dimensional folding of the polypeptide chain (discontinuous epitopes), of post-translational modifications of a protein or of a combination thereof.

The term "therapeutic target" refers to nucleotide or peptide sequences against which a drug or therapeutic compound can be designed and applied.

The term "antagonist" refers to any molecule that inhibits the biological activity of the antagonised molecule. Examples of antagonist molecules include proteins, peptides, variations of natural peptide sequences, small organic molecules (usually molecules with a molecular weight under 500 Daltons), etc.

Sp1 as a Marker of NASH and/or Target for Drug Screening

The invention is based on the finding that the regulation of the proteins responsible for Sp1 phosphorylation and the concentration (level) of phosphorylated Sp1 protein are increased in liver tissue samples from NASH patients but not in liver tissue samples from NASH free subjects.

As it has been previously mentioned, the inventors, looking for the presence of consensus sequences for all vertebrate transcription factors listed in the Gene Regulation database (http://www.gene-regulation.com/) among the promoters of the genes listed in Table 1 (EP 04103540.3), found that only Sp1 transcription factor was present significantly in the promoters of 34 of the genes listed in said Table 1, suggesting that phosphorylation of Sp1 may be involved in the underlying mechanisms that lead to NASH. Sp1 is among the transcription factors that are redox-activated. Since 10 of the NASH-associated genes identified here encode for proteins localized in the mitochondria and MAT1A-KO mice have mitochondrial dysfunction and oxidative stress, it seems that activation of Sp1 may be involved in the underlying mechanisms that lead to NASH.

Table I includes the 85 discriminative gene markers specific of NASH in human liver tissue samples which constitute the genomic signature or fingerprint of NASH in humans, disclosed in Table 1 of EP 04103540.3. Said Table I also includes an indication of the genes which promoters contain a Sp1 binding site.

TABLE I

| NAME | DESCRIPTION | HE | SP1 |
|---|---|---|---|
| | Apoptosis regulador | | |
| Bag1 | Bcl2-associated athanogene 1 | + | Y |
| | Chaperone | | |
| Bag1 | Bcl2-associated athanogene 1 | + | Y |
| Wbscr18 | Similar to syntaxin 1A (brain) | + | |
| | Defense/immunity protein__Blood coagulation factor | | |
| F11 | Coagulation factor XI | − | |
| | Enzyme__Hydrolase | | |
| 1300019N10Rik | Clone: 1300019N10, hypothetical protein | − | |
| 2310010M10Rik* | Similar to cytidine and dCMP deaminase domain containing 1 (NYD-SP15) | + | |
| Ahcy11 | S-adenosylhomocysteine hydrolase-like 1 | − | |
| AI507170* | Similar to platelet-activating factor acetylhydrolase 2, 40 kDa (PAFAH2) | + | |
| Apex1 | Apurinicapyrimidinic endonuclease | + | |
| BC026374* | Similar to carboxylesterase 2 (CES2) | − | |
| Dnase1l3 | Deoxyribonuclease 1-like 3 | + | |
| Es10 | Esterase 10 | − | |
| F11 | Coagulation factor XI | − | |
| Gna14 | Guanine nucleotide binding protein, alpha 14 | − | |
| Pgls | Similar to 6-phosphogluconolactonase | − | |
| Psma6 | Proteasome (prosome, macropain) subunit, alpha type 6 | + | |
| | Enzyme__Isomerase | | |
| Hpgd | Similar to hydroxyprostaglandin dehydrogenase 15-(NAD) | + | |
| Ptges | Prostaglandin E synthase | − | Y |
| | Enzyme__Kinase | | |
| 2310010M10Rik* | Similar to cytidine and dCMP deaminase domain containing 1 (NYD-SP15) | + | |
| Frap1 | FK506 binding protein 12-rapamycin associated protein 1 | − | |
| Galk1 | Galactokinase | + | Y |
| Pip5k1b | Similar to phosphatidylinositol-4-phosphate 5-kinase, type 1 beta | + | |
| | Enzyme__Ligase | | |
| Asns | Asparagine synthetase | − | Y |
| | Enzyme__Lyase | | |
| Aco2 | Similar to Aconitase 2, mitochondrial | + | Y |
| Apex1 | Apurinicapyrimidinic endonuclease | + | |
| Umps | Uridine monophosphate synthetase | + | |
| | Enzyme__Monooxygenase | | |
| Cyp2a5 | Cytochrome P450, 2a5 | − | |
| Cyp4f14 | Cytochrome P450, subfamily IVF, polypeptide 14 (leukotriene B4 omega hydroxylase) | *** | |
| | Enzyme__Oxidoreductase | | |
| Cyp2a5 | Cytochrome P450, 2a5 | − | |
| Cyp4f14 | Cytochrome P450, subfamily IVF, polypeptide 14 (leukotriene B4 omega hydroxylase) | *** | |
| Decr1 | 2,4-dienoyl CoA reductase 1, mitochondrial | + | |
| Gpd1 | Glycerol phosphate dehydrogenase 1, cytoplasmic adult | + | Y |
| Hao1 | Hydroxyacid oxidase 1, liver | + | |
| Hpgd | Similar to hydroxyprostaglandin dehydrogenase 15-(NAD) | + | |
| Mthfr | Similar to 5,10-methylenetetrahydrofolate reductase (NADPH) | − | Y |
| | Enzyme__Transferase | | |
| 4930479F15Rik* | Similar to hydroxyacyl-Coenzyme A dehydrogenase/3-ketoacyl-Coenzyme A | + | Y |

TABLE I-continued

| NAME | DESCRIPTION | HE | SP1 |
|---|---|---|---|
| | thiolase/enoyl-Coenzyme A hydratase, beta subunit (HADHB) | | |
| Acat1 | Similar to Acetyl-Co A acetyltransferase 1 | + | Y |
| ACTL | Acetyl CoA transferase-like protein (ACAT2) | + | Y |
| Cmas | CMP-N-acetylneuraminic acid synthetase | + | |
| Dlat | Similar to Dihydrolipoamide S-acetyltransferase (E2 component of pyruvate dehydrogenase complex) | + | Y |
| Frap1 | FK506 binding protein 12-rapamycin associated protein 1 | − | |
| Galk1 | Galactokinase | + | Y |
| Gstm2 | Glutathione S-transferase, mu 2 | − | |
| Gstm4 | Glutathione transferase GSTM7-7 | − | Y |
| Pip5k1b | Similar to phosphatidylinositol-4-phosphate 5-kinase, type 1 beta | + | |
| Shmt2 | Similar to serine hydroxymethyltransferase 2 (mitochondrial) | − | |
| Umps | Uridine monophosphate synthetase | + | |
| | Enzyme regulator__Enzyme activator | | |
| 1190002H23Rik* | Similar to response gene to complement 32 (RGC32) | + | |
| | Enzyme regulator__Kinase regulador | | |
| 1190002H23Rik* | Similar to response gene to complement 32 (RGC32) | + | |
| | Ligand binding or carrier | | |
| Mrs3/4-pending | Similar to putative mitochondrial solute carrier (MRS3/4) | + | Y |
| Slc25a5 | Solute carrier family 25 (mitochondrial carrier; adenine nucleotide translocator) | + | |
| | Ligand binding or carrier__Calcium binding | | |
| 1110030N17Rik* | Similar to mitochondrial Ca2+-dependent solute carrier (MCSC) | − | |
| Cab39 | Calcium binding protein, 39 | + | Y |
| Rgn | Regucalcin | + | Y |
| S100a10 | S100 calcium binding protein A10 (calpactin) | + | |
| | Ligand binding or carrier__Heavy metal binding | | |
| 2310010M10Rik* | Similar to cytidine and dCMP deaminase domain containing 1 (NYD-SP15) | + | |
| Aco2 | Similar to Aconitase 2, mitochondrial | + | Y |
| | Ligand binding or carrier__Nucleic acid binding | | |
| 2810480G15Rik | Expressed sequence AI503051 | − | Y |
| 4633401C23Rik* | Similar to Zinc finger protein 565 (FLJ36991) | − | |
| Apex1 | Apurinicapyrimidinic endonuclease | + | |
| Dnase1l3 | Deoxyribonuclease 1-like 3 | + | |
| LOC228980 | TAF4A RNA polymerase II, TATA box binding protein (TBP)-associated factor 135 kDa | − | Y |
| Pparg | Peroxisome proliferator activated receptor gamma | + | |
| Rbpms | RNA binding protein gene with multiple splicing | + | |
| | Ligand binding or carrier__Nucleotide binding | | |
| 2610313E07Rik* | Similar to ADP-ribosylation factor-like 10C (FLJ10702) | + | |
| Galk1 | Galactokinase | + | Y |
| Gna14 | Guanine nucleotide binding protein, alpha 14 | − | |
| Gpd1 | Glycerol phosphate dehydrogenase 1, cytoplasmic adult | + | Y |
| Slc2a1 | Solute carrier family 2 (facilitated glucose transporter), member 1 | − | |
| | Ligand binding or carrier__Protein binding | | |
| 1190002H23Rik* | Similar to response gene to complement 32 (RGC32) | + | |

TABLE I-continued

| NAME | DESCRIPTION | HE | SP1 |
|---|---|---|---|
| Bag1 | Bcl2-associated athanogene 1 | + | Y |
| Cdc37l | Cell division cycle 37 homolog (*S. cerevisiae*)-like (HARC) | + | Y |
| Fcgrt | Fc receptor, IgG, alpha chain transporter | + | Y |
| | Ligand binding or carrier__Transcription factor | | |
| LOC228980 | TAF4A RNA polymerase II, TATA box binding protein (TBP)-associated factor 135 kDa | − | Y |
| Pparg | Peroxisome proliferator activated receptor gamma | + | |
| | Signal transducer | | |
| Gna14 | Guanine nucleotide binding protein, alpha 14 | − | |
| | Signal transducer__Receptor | | |
| 5031409J19Rik | RIKEN cDNA 5031409J19 gene | + | |
| Fcgrt | Fc receptor, IgG, alpha chain transporter | + | Y |
| Pparg | Peroxisome proliferator activated receptor gamma | + | |
| | Translation regulador | | |
| Pparg | Peroxisome proliferator activated receptor gamma | + | |
| | Transporter | | |
| C730032N17Rik | Similar to solute carrier family 17 (sodium phosphate), member 2 | − | |
| Slc25a5 | Solute carrier family 25 (mitochondrial carrier; adenine nucleotide translocator) | + | |
| | Transporter__Carbohydrate transporter | | |
| Slc2a1 | Solute carrier family 2 (facilitated glucose transporter), member 1 | − | |
| | Transporter__Carrier | | |
| Slc2a1 | Solute carrier family 2 (facilitated glucose transporter), member 1 | − | |
| | Transporter__Electron transporter | | |
| Hpgd | Similar to hydroxyprostaglandin dehydrogenase 15-(NAD) | + | |
| Hao1 | Hydroxyacid oxidase 1, liver | + | |
| | Transporter__Protein transporter | | |
| Snx5 | Sorting nexin 5 | − | |
| | Unkown molecular function | | |
| 0610010K14Rik | Myb-like DNA-binding domain containing protein | + | Y |
| 1110007C05Rik* | Similar to hypothetical transmembrane protein SBBI54 | − | |
| 1810018L08Rik | Socs-5 | + | |
| 2010313D22Rik | RIKEN cDNA 2510002A14 gene | − | |
| 2400006A19Rik* | Similar to proteasome regulatory particle subunit P44s10 | + | |
| 2810428F02Rik* | Similar to transmembrane protein 19 (FLJ10936) | + | |
| 3110005G23Rik | Similar to RIKEN cDNA 3110005G23 gene, MGC: 28055 | − | |
| 4930422J18Rik* | Similar to SPRY domain-containing SOCS box protein SSB-1 | + | Y |
| 9130414A06Rik | Heterogeneous nuclear ribonucleoprotein A2B1 (HNRPA2B1) | + | Y |
| Bcl7c* | Similar to glutamate dehydrogenase 1 (GLUD1) | + | Y |
| Cd81 | CD 81 antigen | + | Y |
| D530030D03Rik* | Similar to HSPC163 protein | + | |
| Dnajd1 | DnaJ (Hsp40) homolog, subfamily D, member 1 | + | |
| Fbxl10 | F-box protein FBL10 | − | Y |
| Gga2 | Homolog to ADP-ribosylation factor binding protein GGA2 (Gamma-adaptin related protein 2) | − | Y |
| Idb4 | Inhibitor of DNA binding 4 (ID4) | − | Y |
| Il17rl | Interleukin 17 receptor-like | + | Y |

TABLE I-continued

| NAME | DESCRIPTION | HE | SP1 |
|---|---|---|---|
| LOC216892* | Similar to MYB binding protein (P160) 1a (MYBBP1A) | − | Y |
| Perp-pending | P53 apoptosis effector related to Pmp22 (PIGPC1) | + | Y |
| Rpa3 | Similar to replication protein A3, 14 kDa | + | |
| Rtn4 | Homolog to GLUT4 VESICLE 20 KDA PROTEIN | + | Y |
| SELENBP1** | Similar to Chromosome 14 open reading frame 52 | + | |
| Sgce | Sarcoglycan, epsilon | + | Y |
| Tere1-pending* | Similar to transitional epithelia response protein (TERE1) | − | Y |
| Tsap6-pending* | Similar to Dudulin 2 (TSAP) | − | Y |
| Ttc3 | Tetratricopeptide repeat domain | − | |

HE = Human expression
Sp1 = "Y" means presence of the consensus sequence to bind Sp1

Since it has been shown that genes that are co-expressed in multiple microarray data sets have functional relationships (Lee et al., Co-expression analysis of human genes across many microarray data sets. Genome Res 14:1085-1094 (2004)), further analysis of the genes identified in the genomic signature of NASH should give greater insight in the underlying mechanism of NASH. In order to identify in vivo Sp1 target sequences, a chromatin immunoprecipitation (ChIP) assay was carried out (Example 1). Briefly, liver chromatin from wild type (WT) and MAT1A-KO mice was immunoprecipitated with an anti-Sp1 antibody and the genomic DNA was subsequently used for PCR amplification with specific primers for those genes identified whose promoters had a potential Sp1 binding site. The results (FIG. 1) show that Sp1 binds to the promoters of said 11 genes, being the binding of Sp1 to the promoters of said 11 genes enhanced in MAT1A-KO mice liver as compared to WT mice liver. The expression of 9 of said 11 genes (ID4, PIGPC1, MTHFR, PTGES, SSB1, HNRPA2B1, MRS3, HARC and GSTM) was enhanced in MAT1A-KO mice liver as compared to the expression thereof in WT mice liver. However, the expression levels of 2 genes (RGN and GGa2) was similar in livers of WT and MAT1A-KO mice. Furthermore, Sp1 phosphorylation seems to be mediating the activation of said genes (Example 2) because Sp1 protein is found in a higher phosphorylated state in liver tissue samples from MAT1A-KO mice than in liver tissue samples from WT mice (FIG. 2).

Diagnostic and Prognostic Methods

As it has been previously mentioned, the present invention is based on the finding that the phosphorylation state of Sp1 protein is increased in liver tissue samples from NASH patients but not in liver tissue samples from NASH free subjects. In fact, subjects diagnosed with NASH present, in liver tissue samples, high levels of phosphorylated Sp1 relative to the levels in liver samples from NASH free subjects (i.e., subjects without a clinical history of NASH or control subjects).

Accordingly, the evaluation and comparison of the levels of phosphorylated Sp1 protein in liver tissue samples can be both diagnostic or prognostic of NASH. For example, an elevated level of phosphorylated Sp1 protein in a liver tissue sample is indicative of NASH or a greater risk or predisposition of the subject to develop NASH. Therefore, the above mentioned finding can be used in one or more of the following methods: diagnostic assays, prognostic assays, monitoring clinical trials and screening assays as further described herein.

Thus, the invention further provides diagnostic and prognostic assays for detecting phosphorylated Sp1 proteins. Also provided are diagnostic and prognostic assays for detecting interactions between phosphorylated Sp1 and Sp1 target molecules, particularly antagonists.

Therefore, in an aspect, the invention relates to an in vitro method to detect NASH in a subject, or to determine the stage or severity of said condition in a subject, or to determine the predisposition of a subject to develop NASH, or to monitor the effect of the therapy administered to a subject with said condition, hereinafter referred to as the method of the invention, which comprises:

a) quantifying the level of phosphorylated Sp1 protein in a liver tissue sample from said subject, and;

b) comparing said level to that of a control sample;

wherein an increase in said level relative to that of the control is indicative of NASH, i.e., it is an indication that said subject is suffering from NASH or has a predisposition to develop NASH. The level of phosphorylated Sp1 protein in a liver tissue sample as compared to that of a liver tissue control sample can also indicate the stage or severity of NASH in a subject, or can be useful for monitoring the effect of the therapy administered to a subject with said condition.

In order to carry out the method of the invention, a sample is obtained from the subject under study. In a particular embodiment, the sample is a liver tissue sample, which can be obtained by conventional methods, e.g., by biopsy, by using methods well known to those of ordinary skill in the related medical arts. Methods for obtaining the sample from the biopsy include gross apportioning of a mass, or microdissection or other art-known cell-separation methods. Samples can be obtained from subjects previously diagnosed or not with NASH, or from subjects who are receiving or have previously received anti-NASH treatment.

Because of the variability of the cell types in diseased-tissue biopsy material, and the variability in sensitivity of the diagnostic methods used, the sample size required for analysis may range from 1, 10, 50, 100, 200, 300, 500, 1,000, 5,000, 10,000, to 50,000 or more cells. The appropriate sample size may be determined based on the cellular composition and condition of the biopsy. The standard preparative steps for said determination are well known to one of ordinary skill in the art.

In a particular embodiment, with the aim of quantifying the phosphorylation of Sp1 protein, the method of the invention comprises (i) contacting the protein extract extracted from the sample with a composition comprising one or more antibodies specific for one or more epitopes of phosphorylated Sp1 protein, and (ii) quantifying the complexes Sp1-antibodies formed. There is a wide range of immunological assays (immunoassays) available to detect and quantify the formation of specific antigen-antibody complexes; a number of protein-binding assays, competitive and non-competitive, have been previously described, and several of these are commercially available. Hence, the amount of phosphorylated Sp1 protein can be quantified by means of specific antibodies to phosphorylated Sp1, i.e., antibodies which recognize (or bind) phosphorylated Sp1, such as, phospho-specific antibodies, antibodies which recognize any epitope on phosphorylated Sp1 protein, for example, antibodies that recognize the binding between the phosphorylation site (e.g., a serine, threonine or tyrosine residue) and a phosphorus-containing moiety, or any epitope, for example, a conformational epitope, generated in the phosphorylated Sp1 protein as a result of the phosphorylation of Sp1. Said antibodies can be in the form of monoclonal antibodies, polyclonal antibodies, intact or recombinant fragments of antibodies, combibodies and Fab or scFv of antibody fragments. These antibodies can be human, humanised or non-human in origin. The antibodies used in these assays can be labelled or unlabelled; the unlabelled antibodies can be used in agglutination assays; the labelled antibodies can be used in a wide range of assays. Antibody labels include radionucleotides, enzymes, fluorophores, chemiluminescent reagents, enzyme substrates or cofactors, enzyme inhibitors, particles, colorants and derivatives. There is a wide variety of assays well known to those skilled in the art that can be applied to the present invention, which use unlabelled antibodies as primary reagents and labelled antibodies as secondary reagents. These techniques include but are not limited to Western-blot or Western transfer, ELISA (Enzyme-linked immunosorbent assay), RIA (Radioimmunoassay), Competitive EIA (Competitive enzyme immunoassay), DAS-ELISA (Double antibody sandwich-ELISA), immunocyto-chemical and immunohistochemical techniques, techniques based on biochips or protein microarrays that use specific antibodies, and colloidal precipitation-based assays in formats such as dipsticks. Other techniques to detect and quantify the phosphorylation of Sp1 protein are affinity chromatography, ligand binding assays and lectin binding assays.

The final step of the method of the invention involves comparing the level of phosphorylated Sp1 protein quantified in a liver tissue sample from the subject under study to the level of phosphorylated Sp1 protein in a liver tissue control sample (i.e., baseline level or reference value). The levels of phosphorylated Sp1 protein in liver tissue control samples can be determined by measuring levels of phosphorylated Sp1 protein in a liver tissue sample from NASH free subjects (i.e., control subjects with respect to NASH). An increase in the level of phosphorylation of Sp1 protein in a liver tissue sample from the subject under study relative to the level of Sp1 protein in a liver tissue control sample is indicative of NASH, i.e., it is an indication that said subject is suffering from NASH or has a predisposition to develop NASH. Further, the level of phosphorylated Sp1 protein in a liver tissue sample as compared to that of a liver tissue control sample can also indicate the stage or severity of NASH in a subject, or can be useful for monitoring the effect of the therapy administered to a subject with said condition.

The method of the invention, based on the measurement of the level (concentration) of phosphorylated Sp1 protein in liver tissue samples is highly sensitive and specific.

In other aspect, the invention refers to the use of a phosphorylated Sp1 protein or a peptide sequence derived from a phosphorylated Sp1 protein to in vitro detect or diagnose NASH in a subject, or to determine the stage or severity of said condition in a subject, or to determine the predisposition of a subject to develop NASH, or to monitor the effect of the therapy administered to a subject with said NASH.

Drug Screening Assays

The invention also provides a method (also referred to herein as a "screening assay") for identifying candidate agents (e.g., small molecules, nucleic acids, peptides, antibodies, peptidomimetics or other drugs) which have a modulatory effect on, for example, Sp1 expression or on Sp1 biological activity.

Therefore, another aspect of the invention relates to an in vitro method for identifying and/or evaluating the efficacy of a potentially therapeutic agent against NASH, which comprises:

a) contacting a culture of liver cells with a test compound under the appropriate conditions and for the required period of time for them to interact;

b) determining the level of phosphorylated Sp1 protein;

c) comparing said level obtained in step b) to that of a control culture of liver cells lacking said test compound; and d) selecting a test compound which causes said level of step b) to decrease.

The selected compounds can be used, for example, for further testing as a potential agent for the prophylactic and/or therapeutic treatment of NASH.

The determination (detection and quantification) of the levels of phosphorylated Sp1 protein can be performed in a similar manner to that described in connection with the method of the invention.

Since phosphorylated Sp1 activates the expression of some genes, and increased levels of phosphorylated Sp1 protein are found in liver tissue samples from subjects suffering from NASH or having a greater risk or predisposition to develop NASH, an agent that decreases the levels of phosphorylated Sp1 protein or that reverses the effects of increased levels thereof, for example, by inhibiting or reducing the phosphorylation of Sp1 protein, becomes a candidate for NASH therapy (prophylaxis and/or treatment). Agents that are found by using the screening assays provided by the instant invention to be capable of decreasing Sp1 activity by at least 5%, more preferably by at least 10%, still more preferably by at least 30%, still more preferably by at least 50%, still more preferably by at least 70%, even more preferably by at least 90%, may be selected for further testing as a prophylactic and/or therapeutic anti-NASH agent. Sp1 and phosphorylated Sp1 can be determined by conventional techniques, e.g., by Western blotting.

Agents that are found to be capable of decreasing Sp1 activity may be used, for example, to reduce the symptoms of NASH alone or in combination with other appropriate agents or treatments.

In another aspect, the invention relates to the use of a phosphorylated Sp1 protein or a peptide sequence derived from Sp1 in a method for screening for, identifying, developing and/or evaluating the efficacy of potentially therapeutic compounds against NASH. In a particular embodiment, peptides comprising phosphorylation sites of phosphorylated Sp1 protein can be used as antigens in order to obtain antibodies against phosphorylated Sp1 protein. Recently, screening methods based on competitive or non-competitive binding of the molecule with therapeutic potential to the therapeutic target have attracted much attention.

Another aspect of this invention relates to an agent, hereinafter referred to as agent of the invention, characterised by its ability to inhibit expression and/or activity and/or phosphorylation of the Sp1 protein. Said agent, which can be identified and evaluated according to the present invention, can be selected from the following:

a) a compound which inhibits phosphorylation of Sp1 protein in liver,
b) a cytotoxic agent, such as a toxin, a molecule with radioactive atoms or chemotherapeutic agents, including but not limited to small organic and inorganic molecules, peptides, phosphopeptides, antisense molecules, ribozymes, triple-helix molecules, double stranded RNA etc., which inhibits the expression and/or the activity and/or the phosphorylation of the Sp1 protein,
c) an antibody, or combination of antibodies, specific for one or more epitopes on the phosphorylated Sp1 protein, preferably a human or humanised monoclonal antibody, including fragments thereof, single-chain antibodies and anti-idiotype antibodies, and
d) an antagonist compound of the phosphorylated Sp1 protein which inhibits one or more of the functions of the Sp1 protein.

In a particular embodiment, the agent of the invention is an antibody specific for phosphorylated Sp1 protein, sometimes referred herein as antibody of the invention. Such antibodies include polyclonal antibodies, monoclonal antibodies, Fab and single chain Fv (scFv) fragments thereof, bispecific antibodies, heteroconjugates, human and humanized antibodies. Such antibodies may be produced in a variety of ways, including hybridoma cultures, recombinant expression in bacteria or mammalian cell cultures, and recombinant expression in transgenic animals. There is abundant guidance in the literature for selecting a particular production methodology, e.g., Chadd and Chamow, Curr. Opin. Biotechnol., 12:188-194 (2001). The choice of manufacturing methodology depends on several factors including the antibody structure desired, the importance of carbohydrate moieties on the antibodies, ease of culturing and purification, and cost. Many different antibody structures may be generated using standard expression technology, including full-length antibodies, antibody fragments, such as Fab and Fv fragments, as well as chimeric antibodies comprising components from different species. Antibody fragments of small size, such as Fab and Fv fragments, having no effector functions and limited pharmokinetic activity may be generated in a bacterial expression system. Single chain Fv fragments show low immunogenicity and are cleared rapidly from the blood.

The antibodies of the present invention may be polyclonal antibodies. Such polyclonal antibodies can be produced in a mammal, for example, following one or more injections of an immunizing agent, and preferably, an adjuvant. Typically, the immunizing agent and/or adjuvant will be injected into the mammal by a series of subcutaneous or intraperitoneal injections. The immunizing agent may include phosphorylated Sp1 or a fragment thereof or a fusion protein thereof. Alternatively, a crude protein preparation which has been enriched for a phosphorylated Sp1 protein or a fragment thereof can be used to generate antibodies. Such proteins, fragments or preparations are introduced into the non-human mammal in the presence of an appropriate adjuvant. If the serum contains polyclonal antibodies to undesired epitopes, the polyclonal antibodies are purified by immunoaffinity chromatography.

Alternatively, said antibodies may be monoclonal antibodies. Monoclonal antibodies may be produced by hybridomas, wherein a mouse, hamster, or other appropriate host animal, is immunized with an immunizing agent to elicit lymphocytes that produce or are capable of producing antibodies that will specifically bind to the immunizing agent, e.g. Kohler and Milstein, Nature 256:495 (1975) The immunizing agent will typically include the phosphorylated Sp1 protein or a fragment thereof or a fusion protein thereof and optionally a carrier. Alternatively, lymphocytes may be immunized in vitro. Generally, spleen cells or lymph node cells are used if non-human mammalian sources are desired, or peripheral blood lymphocytes ("PBLs") are used if cells of human origin are desired. The lymphocytes are fused with an immortalized cell line using a suitable fusing agent, such as polyethylene glycol, to produce a hybridoma cell. In general, immortalized cell lines are transformed mammalian cells, for example, myeloma cells of rat, mouse, bovine or human origin. The hybridoma cells are cultured in a suitable culture medium that preferably contains one or more substances that inhibit the growth or survival of unfused, immortalized cells. The culture medium (supernatant) in which the hybridoma cells are cultured can be assayed for the presence of monoclonal antibodies directed against phosphorylated Sp1 protein by conventional techniques, such as by immunoprecipitation or by an in vitro binding assay, such as RIA or ELISA.

The monoclonal antibodies may also be made by recombinant DNA methods, such as those described in U.S. Pat. No. 4,816,567. DNA encoding the monoclonal antibodies of the invention can be isolated from the phosphorylated Sp1-specific hybridoma cells and sequenced, e.g., by using oligonucleotide probes that are capable of binding specifically to genes encoding the heavy and light chains of murine antibodies. Once isolated, the DNA may be inserted into an expression vector, which is then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for the murine heavy and light chain constant domains for the homologous human sequences, or by covalently joining to the immunoglobulin coding sequence all or part of the coding sequence for a non-immunoglobulin polypeptide. The non-immunoglobulin polypeptide can be substituted for the constant domains of an antibody of the invention, or can be substituted for the variable domains of one antigen-combining site of an antibody of the invention to create a chimeric bivalent antibody.

The antibodies may also be monovalent antibodies. Methods for preparing monovalent antibodies are well known in the art. For example, in vitro methods are suitable for preparing monovalent antibodies. Digestion of antibodies to produce fragments thereof, particularly, Fab fragments, can be accomplished using routine technniques known in the art.

Antibodies and antibody fragments characteristic of hybridomas of the invention can also be produced by recombinant means by extracting messenger RNA, constructing a cDNA library, and selecting clones which encode segments of the antibody molecule.

The antibodies of the invention may further comprise humanized antibodies or human antibodies. The term "humanized antibody" refers to humanized forms of non-human (e.g., murine) antibodies that are chimeric antibodies, immunoglobulin chains or fragments thereof (such as Fv, Fab, Fab', F (ab'), or other antigen-binding partial sequences of antibodies) which contain some portions of the sequence derived from non-human antibodies. Humanized antibodies include human immunoglobulins in which residues from a complementary determining region (CDR) of the human immunoglobulin are replaced by residues from a CDR of a non-human species such as mouse, rat or rabbit having the desired binding specificity, affinity and capacity. In general, the humanized antibody will comprise substantially all of at least one, and generally two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. Methods for humanizing non-human antibodies are well known in the art. Generally, a humanized antibody has one or more amino acids introduced into it from a source which is non-human in order to more closely resemble a human antibody, while still retaining the original binding activity of the antibody.

Heteroconjugate antibodies which comprise two covalently joined antibodies, are also within the scope of the present invention. Heteroconjugate antibodies may be prepared in vitro using known methods in synthetic protein chemistry, including those involving crosslinking agents. For example, immunotoxins may be prepared using a disulfide exchange reaction or by forming a thioether bond.

The antibodies of the invention are preferably specific for the phosphorylated Sp1 protein and so, do not bind peptides derived from other proteins with high affinity. Said antibodies may be used as functional modulators, most commonly as antagonists. Preferably, antibody modulators of the invention are derived from monoclonal antibodies specific for phosphorylated Sp1 protein. Monoclonal antibodies capable of blocking or neutralizing phosphorylated Sp1 protein are generally selected by their ability to inhibit a phosphorylated Sp1 protein biological activity.

Preferably, monoclonal antibodies, Fv fragments, Fab fragments, or other binding compositions derived from monoclonal antibodies of the invention have a high affinity to phosphorylated Sp1 proteins. The affinity of monoclonal antibodies and related molecules to phosphorylated Sp1 proteins may be measured by conventional techniques.

In addition, the antibodies of the present invention are useful for detecting phosphorylated Sp1 proteins. Such detection methods are advantageously applied to diagnosis and/or prognosis of NASH.

Further, the antibodies of the invention can be used to isolate phosphorylated Sp1 proteins by standard techniques, such as affinity chromatography or immunoprecipitation. For example, an antibody of the invention can facilitate the purification of natural phosphorylated Sp1 proteins from cells and of recombinantly produced phosphorylated Sp1 proteins expressed in host cells. Moreover, the antibodies of the invention can be used to isolate phosphorylated Sp1 proteins in order to evaluate the level thereof in a specific tissue, for example, liver tissue. Thus, antibodies of the invention can be used diagnostically to monitor protein levels in tissue as part of a clinical testing procedure, e.g, to determine the efficacy of a given treatment regimen. Detection can be facilitated by coupling (i.e., physically linking) the antibody to a label group.

Another object of the present invention is a pharmaceutical composition comprising an agent of the invention, or a pharmaceutically acceptable salt, derivative or prodrug thereof together with a pharmaceutically acceptable carrier, adjuvant, or vehicle, for administration to a patient. In a particular embodiment, the agent of the invention is an antibody of the invention. The use of an agent of the invention in the manufacture of a pharmaceutical composition to prevent or treat NASH constitutes another aspect of the invention.

Examples of pharmaceutical compositions include any solid (tablets, pills, capsules, granules etc.) or liquid (solutions, suspensions or emulsions) composition for oral, topical or parenteral administration, etc.

The pharmaceutical compositions may be in oral form, either solid or liquid. Suitable dose forms for oral administration may be tablets, capsules, syrops or solutions and may contain conventional excipients known in the art such as binding agents, for example syrup, acacia, gelatin, sorbitol, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulfate. The solid oral compositions may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to methods well known in normal pharmaceutical practice, in particular with an enteric coating.

The pharmaceutical compositions may also be adapted for parenteral administration, such as sterile solutions, suspensions or lyophilized products in the appropriate unit dosage form. Adequate excipients can be used, such as bulking agents, buffering agents or surfactants. The mentioned formulations will be prepared using standard methods such as those described or referred to in the Spanish and US Pharmacopoeias and similar reference texts. Administration of the compounds or compositions of the present invention may be by any suitable method, such as intravenous infusion, oral preparations, and intraperitoneal and intravenous administration. Oral administration is preferred because of the convenience for the patient and the chronic character of the diseases to be treated.

Generally an effective administered amount of a compound of the invention will depend on the relative efficacy of the compound chosen, the severity of the disorder being treated and the weight of the sufferer. However, active compounds will typically be administered once or more times a day for example 1, 2, 3 or 4 times daily, with typical total daily doses in the range of from 0.1 to 1,000 µg/mg/kg/day.

The compounds and compositions of this invention may be used with other drugs to provide a combination therapy. The other drugs may form part of the same composition, or be provided as a separate composition for administration at the same time or at different time.

Another aspect of the instant invention relates to a kit for carrying out the present invention, e.g., diagnostic assay kits, for carrying out the methods disclosed above. In one embodiment, the kit comprises an antibody of the invention that specifically recognizes the phosphorylated Sp1 protein and a carrier in suitable packing. In another embodiment, the kit comprises in packaged combination (a) an antibody of the invention and (b) a conjugate of a specific binding partner for the above monoclonal antibody and a label capable of producing a detectable signal. The reagents may also include ancillary agents such as buffering agents and protein stabilizing agents, e.g., polysaccharides and the like. The kit may further include, when necessary, other members of the signal producing system of which the label is a member, agents for reducing background interference in a test, control reagents, apparatus for conducting a test, and the like. In another embodiment, the diagnostic kit comprises a conjugate of monoclonal antibody of the invention and a label capable of producing a detectable signal. Ancillary agents as mentioned above may also be present.

These kits can be employed to detect the presence of NASH in a subject, or to determine the stage or severity of said condition in a subject or to monitor the effect of the therapy administered to the subject with said conditions.

The following example serves to illustrate the invention.

EXAMPLE 1

Chromatin Immunoprecipitation Assay

1.1 Crosslinked Chromatin Preparation

Liver tissue samples from both control (WT) and MAT1A-KO mice [Lu S C et al. Proc. Natl. Acad. Sci. USA 98:5560-5565 (2001)], at 15 days, 1, 3, 5 and 8 months, were excised and immersed into 10 ml of 1×PBS pH 7.4 and 1% formaldehyde, and gently stirred for 12 minutes at room temperature, in order to crosslink the transcription factors to DNA (crosslinked chromatin). The reactions were stopped by addition of glycine to a final concentration of 0.125 M. The liver tissue samples were washed twice with 10 ml of cold 1×PBS pH 7.4 and immersed into 8 ml of 1×PBS pH 7.4 supplemented with 2 µ/ml of a protease inhibitor cocktail (Sigma). The liver tissues samples were disaggregated with a Dounce homogenizer, passed through a 200 µm pore filter and centrifuged at 1,500 g for 5 minutes. The cell pellets were resuspended in 3 ml of cell lysis buffer (5 mM HEPES pH 8.0, 85 mM KCl, 0.5% NP40) supplemented with a protease inhibitor cocktail (Sigma), incubated on ice for 15 minutes and centrifuged at 3,500 g for 5 minutes to pellet the nuclei. The nuclei pellets were resuspended in nuclear lysis buffer (50 mM Tris HCl pH 8.1, 10 mM EDTA, 1% SDS), supplemented with the same protease inhibitor cocktail mentioned above, at a ratio 1:1 (v:wt) relative to the initial liver tissue weight, incubated on ice for 10 minutes aliquoted in 1 ml fractions and stored at −20° C. or at −80° C. until use for Sp1-ChIP.

1.2 Sp1-CHIP Assay 1 ml of each sample of crosslinked chromatin was sonicated on ice with 7 pulses of 10 s and 40% amplitude in a Vibra-Cell VCX-500 sonicator (Sonics and Materials). The average chromatin size of the fragments obtained was about 500 bp. The sonicated chromatin was centrifuged at 14,000 g for 10 minutes at 4° C. and the supernatants, containing soluble chromatin fragments, were diluted 10-fold with dilution buffer (165 mM NaCl, 0.01% SDS, 1.1% Triton X, 1.2 mM EDTA, 16.7 mM Tris HCl, pH 8.0) supplemented with a protease inhibitor cocktail (Sigma). The diluted chromatin fractions were precleared by adding 30 µL/mL of 1:1 (v/v) protein A/G sepharose (Amersham Biosciences) (previously blocked during 1 hours with 100 µg/mL lambda DNA, 500 µg/mL tRNA and 1 mg/mL BSA) and incubated at 4° C. for 4 hours in a rotating plate. The suspensions were then centrifuged at 14,000 g for 30 s to discard unbound protein A/G sepharose and non-specifically-bound chromatin fragments and the supernatants were fractioned in aliquots equivalent to 50 µg DNA.

The immunofractionation of complexes was performed by adding to each aliquot 2 µg of an anti-Sp1 antibody (Santa Cruz Biotechnology, Inc., Sp1 sc-59) and incubating at 4° C. overnight under rotation in a rotating plate. The samples were then incubated with 50 µl of blocked protein A/G sepharose for 4 hours at 4° C. under gentle rotation and the immunocomplexes, containing chromatin fragments/Sp1-antibody/protein A/G sepharose, were collected by centrifugation at 14,000 g for 30 s, washed twice with low-salt buffer (150 mM NaCl 0.5% deoxycholate, 0.1% SDS, 1% Nonidet P-40, 1 mM EDTA, 50 mM Tris HCl, pH 8.0), twice with high salt buffer (500 mM NaCl 0.5% deoxycholate, 1% Nonidet P-40, 1 mM EDTA, 50 mmM Tris HCl, pH 8.0), twice with LiCl buffer (250 mM LiCl 0.5% deoxycholate, 0.1% SDS, 1% Nonidet P-40, 1 mM EDTA, 50 mM Tris HCl, pH 8.0) and twice with TE buffer (10 mM Tris HCl, 0.25 mM EDTA) pH 8.0. During each washing, the suspension was kept under rotation for 5 minutes at 4° C. An aliquot of the crosslinked chromatin was treated as above, but in the absence of the antibody (NoAb fraction) and the first supernatant, after the preclearing with protein A/G sepharose, was saved as Input fraction. The immunoselected chromatin was eluted from the protein A/G sepharose by two consecutive extractions with 100 µl of elution buffer (1% SDS, 100 mM NaHSO$_3$) each, with 30 s of vigorous shaking in a vortex and centrifugation at 12,000 g for 2 minutes. Both supernatants were combined [immunoprecipitated or IP fraction (Sp1 in FIG. 1)] and incubated at 65° C. overnight to reverse formaldehyde crosslinks. The DNA from all the fractions (NoAb fraction, Input fraction and IP fraction) was extracted after proteinase K incubation and purified with a DNA purification kit (PCR purification kit, Qiagen) and used for PCR analysis of the target genes. Inventors routinely tested the specificity of chromatin immunoprecipitation by checking the presence of Sp1 in the IP fraction by western blotting analysis, carried out with the antibody used to immunoprecipitate the chromatin fragments.

1.3 PCR Analysis of Immunoprecipitated Chromatin

In order to check if the immunoprecipitated chromatin fraction contained genes with the Sp1 bound to the promoter among the DNA pool, the DNA fractions (NoAb fraction, Input fraction and IP fraction) were analyzed by PCR using specific primers for each gene in order to amplify products of 180-300 bp in length, corresponding to either the promoter or coding regions of the target genes. For the analysis 1:5,000 dilutions of the Input fraction and 1:30 of the IP fraction and NoAb fraction were used. PCR analysis of the samples was done by using the following primers:

| Gene | Primer Forward (5'->3') | Primer Reverse (5'->3') |
|---|---|---|
| ID4 | ACAGCGTTGACGGAATGGA<br>SEQ ID NO: 1 | CCGGGTCGCCACAAGA<br>SEQ ID NO: 2 |
| RGN | ATCCCAGGGCCTGGAACA<br>SEQ ID NO: 3 | CCTCTGGGTGTCTGCAGGTT<br>SEQ ID NO: 4 |
| PIPGPC1 | GGCTGGGGGCAATCTG<br>SEQ ID NO: 5 | GACACCGCGACTAAAGGAAGA<br>SEQ ID NO: 6 |

-continued

| Gene | Primer Forward (5'->3') | Primer Reverse (5'->3') |
|---|---|---|
| MTHFR | TCCAGCCGGGAAACCTTACT SEQ ID NO: 7 | TTTGATGGTTCATCCCGATCTG SEQ ID NO: 8 |
| PTGES | TCTGGGTTCCTTCTTGACTTGAG SEQ ID NO: 9 | ACACGGGGACTGAGAGTGAGA SEQ ID NO: 10 |
| SSB1 | AGCGCTGGGTCGGAAAG SEQ ID NO: 11 | GTGGGAGGGCGGAGAAA SEQ ID NO: 12 |
| HNRPA2B1 | ACGTAGTAACACGCCGAGCG SEQ ID NO: 13 | GAACCTTCCCCCCACTAACG SEQ ID NO: 14 |
| GGa2 | AGTATCTTTTCTGGGAACCCTGC SEQ ID NO: 15 | ACACTGAGAGGCACGTGACG SEQ ID NO: 16 |
| MRS3 | CAAAGTAGCTAGAGCGGTTGAGC SEQ ID NO: 17 | CCAGACAGCCATTGGTGTAGG SEQ ID NO: 18 |
| HARC | TACTTCTTCTTCGGCAGTCCG SEQ ID NO: 19 | CGTCTAAGTCACTCTCCTCCTCG SEQ ID NO: 20 |
| GSTM4 | TTGACAGCAGGGTTGAAGTGC SEQ ID NO: 21 | CAGAAGCCAAATTAGGCTCC SEQ ID NO: 22 |
| α-Actin | AGGATTCCTACGTGGGCGAC SEQ ID NO: 23 | TAGAGAGACAGCACCGCCTG SEQ ID NO: 24 |

1.4 Results

Figure 2:
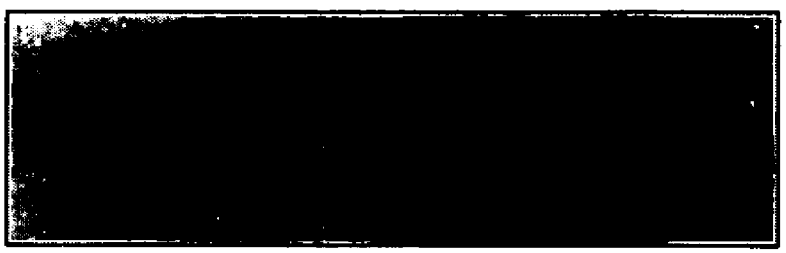
FIG. 2 shows Sp1 phosphorylation in mice liver tissue. Total crude extract from WT and MAT1A-KO mice liver was immunoprecipitated (Ip) with an anti-Sp1 antibody and screened for the presence of phosphoserine with an anti-phosphoserine antibody (upper panel) or screened for total Sp1 content with an antibody against Sp1 (lower panel). The results show that the Sp1 phosphorylation state is increased in liver tissue samples from MAT1A-KO mice versus the Sp1 phosphorilation state in liver tissue samples from WT mice. Lower panel shows that the amount of total Sp1 content screened with an anti-Sp1 antibody is the same in MAT1A-KO and WT mice in the total crude extract.
Figure 2:

The results obtained are shown in FIG. 1. ChIP assay with an anti-Sp1 antibody confirmed that Sp1 binds to the selected gene promoters. From the 11 genes analyzed, the expression of 9 of said genes (ID4, PIGPC 1, MTHFR, PTGES, SSB1, HNRPA2B 1, MRS3, HARC and GSTM) was enhanced in MAT1A-KO mice liver as compared to the expression thereof in WT mice liver, whereas the expression levels of 2 genes (RGN and GGa2) was similar in livers of WT and MAT1A-KO mice.

EXAMPLE 2

Determination of Phosphorylated Sp1 in Mice Liver Tissues 2.1 Immunoprecipitation (IP) of Phosphorylated-SP1

Frozen liver tissue samples from control (WT) and MAT1A-KO mice liver, at 15 days, 1, 3, 5 and 8 months, were homogenized in a buffer containing 10 mM Tris ClH pH 7.6, 5 mM EDTA, 50 mM NaCl, 1% Triton X-100, complete protease inhibitor cocktail (Sigma), and 50 mM NaF. The homogenate was centrifuged for 20 minutes at 40,000 g, and supernatants were collected. Protein (500 µg) was immunoprecipitated with 4 µg of anti-Sp1 antibody (Santa Cruz Biotechnology, Inc., Sp1 sc-59) and 20 µl of Protein A Sepharose 4B (Amersham Pharmacia) in binding buffer containing 150 mM NaCl, 10 mM Tris-HCl, pH 7.6, 1 mM EDTA, 1% deoxycholate, 1% NP-40, 0.25 M LiCl. The samples were rotated overnight at 4° C. The immunoprecipitates were pelleted by centrifugation (1,500 g) and washed 3 times with binding buffer.

2.2 Western Blotting

Immunoprecipitated complexes were dissolved in SDS buffer, separated by SDS-PAGE (7.5%) and analyzed by immunoblotting using commercial antibodies. The immunoblots were developed with a 1:1,000 dilution of an antibody against phosphoserine (Sigma) or against Sp1 (Santa Cruz Biotechnology, Inc., Sp1 sc-59) and a secondary anti-rabbit or anti-mouse antibody conjugated to horseradish peroxidase (Invitrogen) and the luminal-chemiluminescence reagent (ECL, Amersham Biosciences). The processed blots were exposed to X-ray film, and the autoradiograms were analyzed.

2.3 Results

The results of the Western blots are shown in FIG. 2. Upper panel clearly shows that the phosphorylation state of Sp1 is increased in liver samples from MAT1A-KO relative to liver samples from WT. Lower panel shows that the amount of total Sp1 screened with anti-Sp1 antibody is the same in MAT1A-KO and WT in the total crude extract. Consequently, an increased level of phosphorylated Sp1 in liver tissue samples relative to the level of phosphorylated Sp 1 in control liver tissue samples is indicative of NASH.

EXAMPLE 3

Determination of Phosphorylated Sp1 in Human Liver Tissues 3.1 Immunoprecipitation (IP) of Phosphorylated-SP1

This assay was carried out with liver tissue samples from:
normal subjects, i.e., subjects with normal hepatic function with normal liver histology, n=6 (3 female, 3 male; mean age 57.6 years; range 23-79 years); and
NASH diagnosed subjects, namely, NASH grade 1 histologically diagnosed, n=9 (7 female, 2 male; mean age 41.1 years; range 24-61 years) [NASH grade 1 was histologically established (macrovesicular steatosis, lobular, portal inflammation and Mallory bodies) in the absence of other (viral, alcohol, metabolic) causes of NASH [Brunt E M, et al., 1999, Am. J. Gastroenterol. 94, 2467-2474].

Frozen liver tissue samples from both control subjects (i.e., normal subjects) and from NASH diagnosed subjects were homogenized in a buffer containing 10 mM Tris ClH pH 7.6, 5 mM EDTA, 50 mM NaCl, 1% Triton X-100, complete protease inhibitor cocktail (Sigma), and 50 mM NaF. The homogenate was centrifuged for 20 minutes at 40,000 g, and supernatants were collected. Protein (500 µg) was immunoprecipitated with 4 µg of human anti-Sp1 antibody ((H-225): sc-14027, Santa Cruz Biotechnology, Inc) and 20 µl of Protein A Sepharose 4B (Amersham Pharmacia) in binding buffer containing 150 mM NaCl, 10 mM Tris-HCl, pH 7.6, 1 mM EDTA, 1% deoxycholate, 1% NP-40, 0.25 M LiCl. The samples were rotated overnight at 4° C. The immunoprecipitate was pelleted by centrifugation (1,500 g) and washed 3 times with binding buffer.

3.2 Western Blotting

Immunoprecipitated complexes were dissolved in SDS buffer, separated by SDS-PAGE (7.5%) and analyzed by immunoblotting using commercial antibodies. The immunoblots were developed with a 1:1,000 dilution of an antibody against phosphoserine (Sigma) or against Sp1 ((H-225):sc-14027, Santa Cruz Biotechnology, Inc) and a secondary anti-rabbit or anti-mouse antibody conjugated to horseradish peroxidase (Invitrogen) and the luminal-chemiluminescence reagent (ECL, Amersham Biosciences). The processed blots were exposed to X-ray film, and the autoradiograms were analyzed.

3.3 Results

Figure 3:
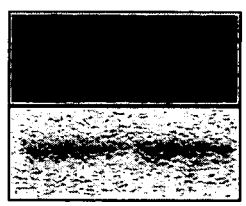
FIG. 3 shows Sp1 phosphorylation in human liver tissues. Total crude extract from human liver tissues from control subjects (CONTROL) and NASH diagnosed subjects (NASH) was immunoprecipitated (Ip) with an anti-phosphoserine antibody and screened for the presence of Sp1 with an anti-Sp1 antibody (upper panel) or was screened for total Sp1 content by using an anti-Sp1 antibody (lower panel) (FIG. 3A). Densitometric changes are shown in FIG. 3B, expressed as fold of induction of Sp1 phosphorylation over control sample value. Differences between NASH and control were statistically significant, $p<0.05$.
Figure 3:
Figure 3:
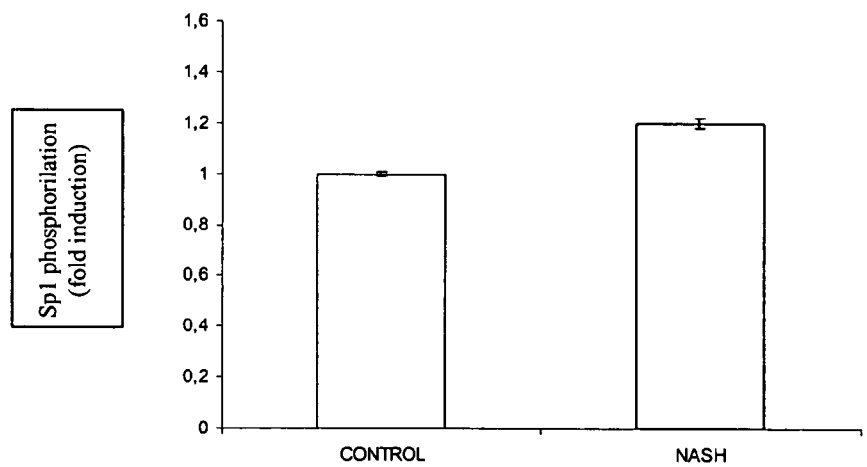

The results of the Western blots are shown in FIG. 3A. Upper panel shows that Sp1 was found to be slightly but significantly (p<0.05) hyperphosphorylated in liver samples from NASH diagnosed subjects as compared to control subjects with normal hepatic function. Lower panel shows that the amount of total Sp1 screened with anti-Sp1 antibody is the same in NASH diagnosed subjects and in control subjects in the total crude extract. Densitometric changes are shown in FIG. 3B, expressed as fold of induction of Sp1 phosphorylation over control sample value. Differences between NASH and control were statistically significant, p<0.05. These results confirm that an increased level of phosphorylated Sp1 in human liver tissue samples relative to the level of phosphorylated Sp1 in control human liver tissue samples is indicative of NASH.

The invention claimed is:

1. An in vitro method for diagnosing or prognosticating non-alcoholic steatohepatitis (NASH) in a subject, said method comprising:
    a) quantifying a level of phosphorylation of Sp1 transcription factor protein in a liver tissue sample from said subject; and
    b) comparing said level to that of a control sample;
wherein a statistically significant increase in said level in the liver tissue sample relative to that of the control is indicative of NASH or a predisposition to NASH in said subject.

2. The method according to claim 1, wherein the liver tissue sample to be analysed is taken from a subject selected from the group consisting of: a subject not previously diagnosed with NASH, a subject who has been previously diagnosed with NASH, a subject receiving anti-NASH treatment, and a subject who has previously received anti-NASH treatment.

3. The method according to claim 1, said method further comprises extracting the liver tissue sample to obtain a protein extract.

4. The method according to claim 3, wherein the quantification of the phosphorylation of Sp1 protein comprises contacting the protein extract with a composition of one or more antibodies specific for one or more epitopes of the phosphorylated Sp1 protein, and quantifying the complexes formed by said specific antibody bound to phosphorylated Sp1 protein.

5. The method according to claim 4, wherein said antibodies are selected from the group consisting of monoclonal antibodies, polyclonal antibodies, intact antibodies, recombinant fragments of antibodies, combibodies, Fab antibody fragments, and scFv antibody fragments.

6. The method according to claim 4, wherein the quantification of said complexes is performed by a technique selected from the group consisting of Western-blotting, ELISA (Enzyme-Linked Immunosorbent Assay), RIA (Radioimmunoassay), Competitive EIA (Competitive Enzyme Immunoassay), DAS-ELISA (Double Antibody Sandwich-ELISA), immunocytochemical techniques, immunohistochemical techniques, techniques based on the use of biochips, techniques based on the use of protein microarrays that include specific antibodies, assays based on the precipitation of colloidal gold in formats, affinity chromatography techniques, and ligand binding assays.

7. The method according to claim 4, wherein the antibody is selected from the group consisting of Sp1 sc-59 and (H-225):sc-14027.

8. The method according to claim 4, wherein said antibodies are selected from the group consisting of human, humanised and non-human in origin.

* * * * *

UNITED STATES PATENT AND TRADEMARK OFFICE
CERTIFICATE OF CORRECTION

PATENT NO. : 7,632,649 B2  Page 1 of 1
APPLICATION NO. : 11/370068
DATED : December 15, 2009
INVENTOR(S) : José María Mato de la Paz It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 547 days.

Signed and Sealed this

Twenty-first Day of December, 2010

David J. Kappos
*Director of the United States Patent and Trademark Office*

```
                        SEQUENCE LISTING

<160> NUMBER OF SEQ ID NOS: 24

<210> SEQ ID NO 1
<211> LENGTH: 19
<212> TYPE: DNA
<213> ORGANISM: Artificial Sequence
<220> FEATURE:
<223> OTHER INFORMATION: Synthetic Construct

<400> SEQUENCE: 1
acagcgttga cggaatgga                                                19

<210> SEQ ID NO 2
<211> LENGTH: 16
<212> TYPE: DNA
<213> ORGANISM: Artificial Sequence
<220> FEATURE:
<223> OTHER INFORMATION: Synthetic Construct

<400> SEQUENCE: 2
ccgggtcgcc acaaga                                                   16

<210> SEQ ID NO 3
<211> LENGTH: 18
<212> TYPE: DNA
<213> ORGANISM: Artificial Sequence
<220> FEATURE:
<223> OTHER INFORMATION: Synthetic Construct

<400> SEQUENCE: 3
atcccagggc ctggaaca                                                 18

<210> SEQ ID NO 4
<211> LENGTH: 20
<212> TYPE: DNA
<213> ORGANISM: Artificial Sequence
<220> FEATURE:
<223> OTHER INFORMATION: Synthetic Construct
```

<400> SEQUENCE: 4
cctctgggtg tctgcaggtt                                            20

<210> SEQ ID NO 5
<211> LENGTH: 16
<212> TYPE: DNA
<213> ORGANISM: Artificial Sequence
<220> FEATURE:
<223> OTHER INFORMATION: Synthetic Construct

<400> SEQUENCE: 5
ggctggcggc aatctg                                                16

<210> SEQ ID NO 6
<211> LENGTH: 21
<212> TYPE: DNA
<213> ORGANISM: Artificial Sequence
<220> FEATURE:
<223> OTHER INFORMATION: Synthetic Construct

<400> SEQUENCE: 6
gacaccgcga ctaaaggaag a                                          21

<210> SEQ ID NO 7
<211> LENGTH: 20
<212> TYPE: DNA
<213> ORGANISM: Artificial Sequence
<220> FEATURE:
<223> OTHER INFORMATION: Synthetic Construct

<400> SEQUENCE: 7
tccagccggg aaaccttact                                            20

<210> SEQ ID NO 8
<211> LENGTH: 22
<212> TYPE: DNA
<213> ORGANISM: Artificial Sequence
<220> FEATURE:
<223> OTHER INFORMATION: Synthetic Construct

<400> SEQUENCE: 8
tttgatggtt catcccgatc tg                                         22

<210> SEQ ID NO 9
<211> LENGTH: 23
<212> TYPE: DNA
<213> ORGANISM: Artificial Sequence
<220> FEATURE:
<223> OTHER INFORMATION: Synthetic Construct

<400> SEQUENCE: 9
tctgggttcc ttcttgactt gag                                        23

<210> SEQ ID NO 10
<211> LENGTH: 21
<212> TYPE: DNA
<213> ORGANISM: Artificial Sequence
<220> FEATURE:
<223> OTHER INFORMATION: Synthetic Construct

<400> SEQUENCE: 10
acaccgggac tgagagtgag a                                          21

<210> SEQ ID NO 11

```
<211> LENGTH: 17
<212> TYPE: DNA
<213> ORGANISM: Artificial Sequence
<220> FEATURE:
<223> OTHER INFORMATION: Synthetic Construct

<400> SEQUENCE: 11
agcgctgggt cggaaag                                                  17

<210> SEQ ID NO 12
<211> LENGTH: 17
<212> TYPE: DNA
<213> ORGANISM: Artificial Sequence
<220> FEATURE:
<223> OTHER INFORMATION: Synthetic Construct

<400> SEQUENCE: 12
gtgggagggc ggagaaa                                                  17

<210> SEQ ID NO 13
<211> LENGTH: 20
<212> TYPE: DNA
<213> ORGANISM: Artificial Sequence
<220> FEATURE:
<223> OTHER INFORMATION: Synthetic Construct

<400> SEQUENCE: 13
acgtagtaac acgccgagcg                                               20

<210> SEQ ID NO 14
<211> LENGTH: 20
<212> TYPE: DNA
<213> ORGANISM: Artificial Sequence
<220> FEATURE:
<223> OTHER INFORMATION: Synthetic Construct

<400> SEQUENCE: 14
gaaccttccc cccactaacg                                               20

<210> SEQ ID NO 15
<211> LENGTH: 23
<212> TYPE: DNA
<213> ORGANISM: Artificial Sequence
<220> FEATURE:
<223> OTHER INFORMATION: Synthetic Construct

<400> SEQUENCE: 15
agtatctttt ctgggaaccc tgc                                           23

<210> SEQ ID NO 16
<211> LENGTH: 20
<212> TYPE: DNA
<213> ORGANISM: Artificial Sequence
<220> FEATURE:
<223> OTHER INFORMATION: Synthetic Construct

<400> SEQUENCE: 16
acactgagag gcacgtgacg                                               20

<210> SEQ ID NO 17
<211> LENGTH: 23
<212> TYPE: DNA
<213> ORGANISM: Artificial Sequence
<220> FEATURE:
<223> OTHER INFORMATION: Synthetic Construct

<400> SEQUENCE: 17
```

```
caaagtagct agagcggttg agc                                            23

<210> SEQ ID NO 18
<211> LENGTH: 21
<212> TYPE: DNA
<213> ORGANISM: Artificial Sequence
<220> FEATURE:
<223> OTHER INFORMATION: Synthetic Construct

<400> SEQUENCE: 18
ccagacagcc attggtgtag g                                              21

<210> SEQ ID NO 19
<211> LENGTH: 21
<212> TYPE: DNA
<213> ORGANISM: Artificial Sequence
<220> FEATURE:
<223> OTHER INFORMATION: Synthetic Construct

<400> SEQUENCE: 19
tacttcttct tccgcagtcc g                                              21

<210> SEQ ID NO 20
<211> LENGTH: 23
<212> TYPE: DNA
<213> ORGANISM: Artificial Sequence
<220> FEATURE:
<223> OTHER INFORMATION: Synthetic Construct

<400> SEQUENCE: 20
cgtctaagtc actctcctcc tcg                                            23

<210> SEQ ID NO 21
<211> LENGTH: 21
<212> TYPE: DNA
<213> ORGANISM: Artificial Sequence
<220> FEATURE:
<223> OTHER INFORMATION: Synthetic Construct

<400> SEQUENCE: 21
ttgacagcag ggttgaagtg c                                              21

<210> SEQ ID NO 22
<211> LENGTH: 20
<212> TYPE: DNA
<213> ORGANISM: Artificial Sequence
<220> FEATURE:
<223> OTHER INFORMATION: Synthetic Construct

<400> SEQUENCE: 22
cagaagccaa attacgctcc                                                20

<210> SEQ ID NO 23
<211> LENGTH: 20
<212> TYPE: DNA
<213> ORGANISM: Artificial Sequence
<220> FEATURE:
<223> OTHER INFORMATION: Synthetic Construct

<400> SEQUENCE: 23
aggattccta cgtgggcgac                                                20

<210> SEQ ID NO 24
<211> LENGTH: 20
<212> TYPE: DNA
```

```
<213> ORGANISM: Artificial Sequence
<220> FEATURE:
<223> OTHER INFORMATION: Synthetic Construct

<400> SEQUENCE: 24
tagagagaca gcaccgcctg                                            20
```